United States Patent [19]

Nozawa et al.

[11] Patent Number: 4,537,967
[45] Date of Patent: Aug. 27, 1985

[54] 1-OXO-1,2,3,4-TETRAHYDRO-3-ISOQUINO-LINE CARBOXYLIC ACID DERIVATIVES

[75] Inventors: Koohei Nozawa, Ohi; Toyokichi Yoshizawa, Isehara; Toshio Kuroda, Sagamihara, all of Japan

[73] Assignee: Wakamoto Pharmaceutical Co., Ltd., Tokyo, Japan

[21] Appl. No.: 510,227

[22] Filed: Jul. 1, 1983

[30] Foreign Application Priority Data

Jul. 8, 1982 [JP] Japan .................. 57-117817

[51] Int. Cl.³ ............................. C07D 217/24
[52] U.S. Cl. .................................. 546/141
[58] Field of Search ......................... 546/141

[56] References Cited

U.S. PATENT DOCUMENTS

| | | | |
|---|---|---|---|
| 3,928,612 | 12/1975 | Sellstedt et al. | 424/258 |
| 3,975,535 | 8/1976 | Buckle et al. | 546/141 |
| 4,046,889 | 9/1977 | Ondetti et al. | 424/244 |
| 4,118,494 | 10/1978 | Kunstmann et al. | 546/141 |
| 4,251,444 | 2/1981 | Freed | 546/141 |
| 4,256,751 | 3/1981 | Hayashi et al. | 546/146 |

Primary Examiner—Glennon H. Hollrah
Assistant Examiner—James H. Turnipseed
Attorney, Agent, or Firm—Weiss & Holloway

[57] ABSTRACT

The following new isocarbostyryl derivatives represented by the general formula [I]:

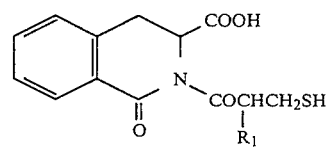

wherein $R_1$ is a hydrogen atom or a lower alkyl group, are provided, said derivatives having excellent angiotensin converting enzyme inhibitory activity with expectations therefore being as a hypotensor, and prepared by solvolysis of a compound of the following general formula [II]:

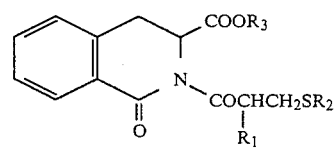

wherein $R_1$ is the same as defined above, $R_2$ is an acyl group, and $R_3$ is a hydrogen atom, an alkyl group or an aralkyl group.

3 Claims, No Drawings

1-OXO-1,2,3,4-TETRAHYDRO-3-ISOQUINOLINE CARBOXYLIC ACID DERIVATIVES

BACKGROUND OF THE INVENTION

The present invention relates to new isocarbostyryl derivatives, in particular derivatives having an excellent inhibitory effect on the angiotensin converting enzyme and to amethod for preparing the derivatives.

The angiotensin converting enzyme (hereinafter referred to as ACE) plays a central role in the physiology of hypertension. It is well known that ACE converts angiotensin I to angiotensin II which has a strong tendency to raise blood pressure.

Therefore, it may be expected that restriction of the ACE action enables the suppression of the increase in blood pressure and various kinds of depressors based on the ACE inhibition have been developed and put into practical use. CAPTOPRIL (INN), MK 421 or the like are known as such a kind of depressor.

SUMMARY OF THE INVENTION

The inventors of this application have carried out exhaustive researches to obtain new compounds having an excellent ACE inhibitory effect, and as a result have found that some isocarbostyryl derivatives have an excellent ACE inhibitory effect and that these derivatives may be expected to be effective as hypertensors.

The principal object of this invention is to provide new isocarbostyryl derivatives, in particular ones having an excellent ACE inhibitory effect.

Another object of this invention is to provide a method of preparation of the isocarbostyryl derivatives having an excellent ACE inhibitory effect.

The above mentioned and other objects of this invention will become obvious by referring to the following detailed explanation.

DETAILED DESCRIPTION OF THE INVENTION

Isocarbostyryl derivatives according to the present invention are represented by the following general formula [I]:

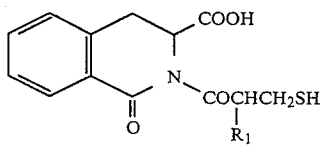

wherein $R_1$ represents a hydrogen atom or a lower alkyl group.

In addition, pharmaceutically acceptable salts of the derivatives such as alkali metal salts, alkaline earth metal salts, ammonium salts or the like naturally fall within the scope of this invention.

These isocarbostyryl derivatives of this invention have an excellent ACE inhibitory effect as will be shown by results of animal tests hereunder disclosed and there are expectations for such derivatives as hypertensors. Among them, the derivatives in which $R_1$ is a hydrogen atom or methyl group have a particularly excellent ACE inhibitory effect.

The compounds [I] of the present invention may be prepared according to the following process which comprises solvolyzing ester bonds of a compound having the following general formula [II]:

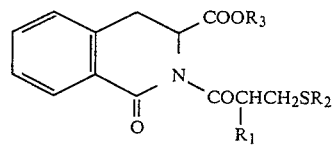

wherein $R_1$ is the same as defined above, $R_2$ represents an acyl group and $R_3$ is a hydrogen atom, an alkyl group or an aralkyl group, under a mild condition so as not to cleave the isoquinoline ring structure.

Among these, preferred are compounds in which $R_1$ is H or methyl, $R_2$ is acetyl, propionyl, butyroyl, isobutyroyl or benzoyl and $R_3$ is H, methyl, ethyl, propyl, tert-butyl or benzyl.

In the reaction, for example, trifluoroacetic acid, propane-2-ol, 2-aminoethanethiol, anisole, a mixture thereof or the like may be used as an agent for solvolysis.

If the ester residue of $R_3$ is an alkyl such as methyl, ethyl, tert-butyl or an aralkyl such as benzyl, it is possible to simultaneously eliminate the ester residue of $R_3$ and the acyl group of $R_2$ by adding trifluoroacetic acid and anisole as the solvolyzing agent and reacting at room temperature for about one hour. If $R_3$ is H and $R_2$ is an acyl group such as acetyl, propionyl, isobutyroyl, benzoyl, the acyl group of $R_2$ may be converted to 2-aminoethanethioacyl group and eliminated, by using a solvent such as acetone, tetrahydrofuran or benzoyl, and 2-aminoethanethiol as the solvolyzing agent and reacting at a temperature of 10° to 30° C. for 1 to 5 hours.

The compounds [II] used in the process for preparing the compounds of the invention as a starting material may advantageously be prepared by, for example, reacting a compound of the general formula [IV]:

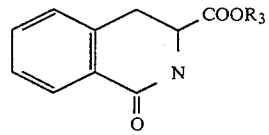

wherein $R_3$ has the same meaning as defined above, with an acid of the general formula [III]:

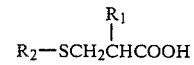

wherein $R_1$ and $R_2$ are the same as defined above, or an active derivative thereof at a temperature of 10° to 30° C. for 1 to 5 hours in an organic solvent, preferably under the presence of a base.

As a base used in the process, there may be mentioned, for example, organic tertiary amines such as triethylamine, tributylamine, pyridine, diisopropylethylamine, N,N-dimethylaniline, N-ethylpiperidine or a mixture thereof.

As the active derivatives of the compound [III] used in the process of this invention, there may be mentioned, for example, acid halides such as acid chlorides, acid bromides; acid anhydrides; a mixed acid anhydride with an alkyl carbonate, in which the alkyl has 1 to 4 carbon atoms, or an inorganic halide such as thionyl chloride, phosphorous oxychloride or phosphorous trichloride; and active esters such as p-nitro-phenyl ester or polychloro-phenyl ester and known active esters such as N,N'-dicyclohexylcarbodiimide.

Preferably, the reaction is carried out by reacting in equivalent molar amounts a compound of the formula [IV] and a compound of the formula [III] in an organic solvent such as methanol, ethanol, benzene, acetonitrile, ethylether, tetrahydrofuran, dioxane or the like, and the reaction is preferably carried out in the presence of at least 2 equivalents of a base.

In the invention, it may be possible to use optically active compounds of the formula [IV] and [III]. In such cases, a corresponding optically active object product [I] may be prepared without causing racemization.

The compounds [I] according to the present invention may be expected to be useful as a hypertensor, since they have an excellent ACE inhibitory effect. This has been well evidenced by an experiment using ACE extracted from rabbit lung and purified. The ACE inhibitory effect of the compounds of the present invention was determined according to the following illustrative test and the results will be shown in the following Table 1.

ILLUSTRATIVE TEST

In this test, male rats (Spraque-Dawleg) of 250 to 350 g in weight were used, which were raised under conditions of free access to food and water.

The day before the test, each rat was narcotized by sodium pentobarbital (50 mg/kg) injected intraperitoneally. A polyethylene tube was inserted into a vein at the groin and fixed in order to introduce angiotensin and, further, another polyethylene tube was inserted into an artery at the groin and fixed to measure the blood pressure thereof. The blood pressure was determined by the use of an electronic sphygmomanometer (Nihon Kohden Kogyo Co., Ltd. type MP-4T).

Each rat was injected with 300 ng/kg of angiotensin I and 100 ng/kg of angiotensin II through the vein at the groin and the blood pressure recorded periodically and the maximum value of the rise in the blood pressure resulting from the injection of angiotensin was determined for use as a control.

Then, the percentage of inhibitory effect was determined by orally administering 13.8 μM/kg of a compound of the invention to each rat, and injecting 300 ng/kg of angiotensin I and 100 ng/kg of angiotensin II into the vein at the groin at periods of 20, 60 or 120 minutes after the administration of the compound, with maximum blood pressures being determined by periodically measuring the blood pressure and comparing each maximum value obtained with that of the controls.

Results obtained are shown in the following Table 1.

TABLE 1

| Compound administered | Inhibition (%) | | |
|---|---|---|---|
| | 20 min | 60 min | 120 min |
| Ex. 1 | 81 | 78 | 59 |
| Ex. 2 | 83 | 70 | 72 |

The invention will now be illustrated in more detail with reference to the following Examples. However, these examples are only for the purpose of illustration.

EXAMPLE 1

(1) 1.1 g of triethyl amine was added to a suspension of 1.0 g of 1-oxo-1,2,3,4-tetrahydro-3-isoquinoline carboxylic acid in 10 ml of acetonitrile. A solution of 3-acetylthiopropionyl chloride (3-acethylthiopropionyl chloride was prepared by adding 1.0 g of thionyl chloride to a solution of 0.8 g of 3-acetylthiopropionic acid in 5 ml of benzene, stirring the solution overnight at room temperature and distilling off the solvent and excess thionyl chloride) in 5 ml of acetonitrile was added drop by drop to the suspension which was ice-cooled. After stirring the mixture for 2 hours at room temperature, the solvent was distilled off, 20 ml of ethylacetate and 10 ml of water were added to the residue and the solution was shaken and the organic phase separated and washed. The organic phase was dried over anhydrous Glauber's salt, the solvent was distilled off and then the residue was recrystalized from benzene to obtain 0.9 g of 2-(3-acetylthiopropionyl)-1-oxo-1,2,3,4-tetrahydro-3-isoquinoline carboxylic acid as a colorless microcrystalline material.

m.p.: 154°–155° C.

M.S. m/e: 321 (M+)

N.M.R. (CDCl$_3$) δ: 8.05 (1H, dd, J=7 Hz, 2 Hz); 7.7–7.1 (3H, m); 5.5 (1H, t, J=4 Hz); 3.6–3.0 (6H, m); 2.23 (3H, s)

I.R. $\nu_{max}^{KBr}$ cm$^{-1}$: 3000–2500, 1695, 1680

(2) 250 mg of 2-aminoethanethiol was added to a solution of 2-(3-acetylthiopropionyl)-1-oxo-1,2,3,4-tetrahydro-3-isoquinoline carboxylic acid (500 mg) in acetonitrile (5 ml), and stirred for 3 hours at room temperature. After distilling off the reaction solvent, 10 ml of ethylacetate and 10 ml of water were added and the solution was shaken and the organic phase separated, and washed with water, dried over anhydrous Glauber's salt and the solvent was distilled off. The product was purified by silicagel column chromatography (benzene-acetic acid; 100:1 V/V) to obtain 95 mg of 2-(3-mercaptopropionyl)-1-oxo-1,2,3,4-tetrahydro-3-isoquinoline carboxylic acid.

m p.: 129.5°–130° C.

M.S. m/e: 279 (M+)

N.M.R. (CDCl$_3$) δ: 8.1 (1H, dd, J=6 Hz, 1.5 Hz); 7.7–7.1 (3H, m); 5.6 (1H, t, J=4 Hz) 3.6–2.9 (6H, m)

EXAMPLE 2

(1) 1.1 g of triethyl amine was added to a suspension of 1-oxo-1,2,3,4-tetrahydro-3-isoquinoline carboxylic acid (1.0 g) in 10 ml of acetonitrile. The suspension was cooled by ice and a solution of 3-acetylthio-2-methyl propionic chloride in 5 ml of acetonitrile was added drop by drop, the 3-acetylthio-2-methyl propionic chloride being prepared by adding 2.0 g of thionyl chloride to a benzene solution of 3-acethylthio-2-methylpropionic acid (0.85 g), stirring overnight at room temperature and distilling off the solvent and the excess amount of thionyl chloride. The mixture was then stirred for two hours at room temperature, the solvent distilled off, 20 ml of ethylacetate and 10 ml of water added, then the solution was shaken and the organic phase separated. After washing the organic phase, it was dried over anhydrous Glauber's salt, the solvent distilled off and then purified by silicagel column chromatography (benzene-acetic acid; 50:1 V/V) to obtain 1.05 g of 2-(3-acetylthio-2-methylpropionyl)-1-oxo-1,2,3,4-tetrahydro-3-isoquinoline carboxylic acid as an oily material.

M.S. m/e: 335 (M+)

N.M.R. (CDCl₃) δ: 8.2 (1H, d, J=7 Hz); 7.6–7.2 (3H, m); 5.5 (1H, m); 4.2 (0.5H, tq, J=7 Hz, 7 Hz); 4.0 (0.5H, tq, J=7 Hz, 7 Hz); 3.5–3.1 (4H, m); 2.31 (1.5H, s); 2.28 (1.5H, s); 1.34 (1.5H, d, J=7 Hz); 1.27 (1.5H, d, J=7 Hz)

(2) 140 mg of 2-aminoethanethiol was added to a solution of 2-(3-acethylthio-2-methylpropionyl)-1-oxo-1,2,3,4-tetrahydro-3-isoquinoline carboxylic acid (300 mg) in 10 ml acetonitrile, and the mixture was stirred for 3 hours at room temperature. After removing the solvent by distillation, 10 ml of ethylacetate and 5 ml of water were added to the residue, the solution was shaken, the organic phase was separated and further washed with water, dried over anhydrous Glauber's salt and the solvent distilled off. The resulting product was purified by silicagel column chromatography (benzene-acetic acid; 100:1 V/V) to obtain 90 mg of 2-(3-mercapto-2-methylpropionyl)-1-oxo-1,2,3,4-tetrahydro-3-isoquinoline carboxylic acid as a colorless oily material.

M.S. m/e: 293 (M+)

N.M.R. (CDCl₃) δ: 8.25 (1H, d, J=7 Hz); 7.7–7.0 (3H, m); 5.76 (1H, t, J=4 Hz); 4.3–3.7 (1H, m); 1.35 (1.5H, d, J=7 Hz); 1.30 (1.5H, d, J=7 Hz)

EXAMPLE 3

(1) 60% sodium hydride (170 mg) was suspended in 5 ml of tetrahydrofuran and a solution of 1-oxo-1,2,3,4-tetrahydro-3-isoquinoline carboxylic acid t-butyl ester (930 mg) in 3 ml of anhydrous tetrahydrofuran was added, while using ice-cooling. A solution of 3-acethylthio-2-methylpropionyl chloride (see example 1) in 5 ml of anhydrous tetrahydrofuran was then added drop by drop. After stirring overnight at room temperature, the solvent was removed by distillation, the residue poured into 20 ml of ice water, extracted with 30 ml of ether, washed with water, dried over anhydrous Glauber's salt and the solvent was then distilled off. After purifying the product by silicagel column chromatography (n-hexane-ethyl acetate; 10:1 V/V), 670 mg of 2-(3-acethylthio-2-methylpropionyl)-1-oxo-1,2,3,4-tetrahydro-3-isoquinoline carboxylic acid t-butyl ester was obtained as a colorless oily material.

M.S. m/e: 391 (M+)

N.M.R. (CDCl₃) δ: 8.2 (1H, d, J=7 Hz); 7.6–7.2 (3H, m); 5.5 (1H, m); 4.2 (0.5H, tq, J=7 Hz, 7 Hz); 4.0 (0.5H, tq, J=7 Hz, 7 Hz); 3.5–3.1 (4H, m); 2.31 (1.5H, s); 2.28 (1.5H, s); 1.34 (1.5H, d, J=7 Hz); 1.27 (1.5H, d, J=7 Hz); 1.22 (4.5H, s); 1.21 (4.5H, s)

(2) t-Butylester of 2-(3-acethylthio-2-methylpropionyl)-1-oxo-1,2,3,4-tetrahydro-3-isoquinoline carboxylic acid was dissolved in 3 ml of trifluoroacetic acid, 1.5 ml of anisole was added, and stirring carried out for 1 hour at room temperature. The trifluoroacetic acid was removed by distillation, the residue was dissolved in 20 ml of ethylacetate, washed with water, dried over anhydrous Glauber's salt and the solvent then distilled off. After purifying the product by silicagel column chromatography (benzene-acetic acid; 50-1 V/V), 370 mg of 2-(3-acethylthio-2-methylpropionyl)-1-oxo-1,2,3,4-tetrahydro-3-isoquinoline carboxylic acid was obtained as a colorless oily material.

The physical properties of the product were completely consistent with those of the compound prepared in Example 2.

The compounds of the present invention act to inhibite angiotensin converting enzyme which converts angiotensin I, produced by the action of the enzyme renin from angiotensinogen, to angiotensin II which acts as a pressor agent. Therefore, these compounds may be expected to be effective in the treatment of hypertension.

For example, when the compounds of the invention are subjected to the measurement of the inhibitory effect according to the method disclosed in Biochemical, Pharmacology, 20, 1637 (1971) by using hippuryl-L-histidine-L-leucine as a substrate, 50% inhibition concentration ($ID_{50}$) is $5.1 \times 10^{-8}$M for 2-(3-mercaptopropionyl)-1-oxo-1,2,3,4-tetrahydro-3-isoquinoline carboxylic acid obtained in Example 1 and $7.3 \times 10^{-8}$M for 2-(3-mercapto-2-methylpropionyl)-1-oxo-1,2,3,4-tetrahydro-3-isoquinoline carboxylic acid in Example 2.

What is claimed is:

1. A compound of the following general formula [I]:

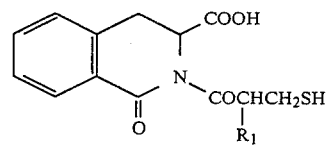

wherein $R_1$ represents a hydrogen atom or a lower alkyl group,
and pharmaceutically acceptable salts thereof.

2. A compound as set forth in claim 1 wherein $R_1$ is a hydrogen atom or methyl group.

3. A compound as set forth in claim 1 or 2 wherein the pharmaceutically acceptable salt is an alkali metal salt, an alkaline earth metal salt or an ammonium salt.

* * * * *